United States Patent [19]

Schlipf

[11] Patent Number: 4,730,481

[45] Date of Patent: Mar. 15, 1988

[54] DEVICE FOR TESTING THE AIR PERMEABILITY OF AN ARTICLE

[75] Inventor: Engelbert Schlipf, Senden, Fed. Rep. of Germany

[73] Assignee: Wurttembergische Filtztuchfabrik D. Geschmay GmbH, Fed. Rep. of Germany

[21] Appl. No.: 35,488

[22] Filed: Apr. 3, 1987

[30] Foreign Application Priority Data

Apr. 5, 1986 [DE] Fed. Rep. of Germany ....... 3611458

[51] Int. Cl.$^4$ ............................................ G01N 15/08
[52] U.S. Cl. .......................................... 73/38; 73/37.7
[58] Field of Search ..................................... 73/38, 37.7

[56] References Cited

U.S. PATENT DOCUMENTS

| | | | |
|---|---|---|---|
| 3,466,925 | 9/1969 | Ziegenhagen et al. | 73/38 |
| 4,311,037 | 1/1982 | Gotchel et al. | 73/38 |
| 4,471,649 | 9/1984 | Cronshaw | 73/38 |
| 4,672,841 | 6/1987 | Schuster et al. | 73/38 |
| 4,676,091 | 6/1987 | Schuster et al. | 73/38 |

Primary Examiner—Stewart J. Levy
Assistant Examiner—Joseph W. Roskos
Attorney, Agent, or Firm—Dick and Harris

[57] ABSTRACT

An improved device for testing the air permeability of an article, particularly felts and screens associated with the manufacture of paper products. The improved device incorporates a measuring channel traversed by air, and inserted into another cylindrical belt channel traversed by air, with both channels attached with their orifices to the test object.

The fan wheel of an anemometer is placed inside the measuring channel to measure the flow rate, the air flow through the measuring channel being non-separating and irrotationally incident on the fan wheel. The measuring channel contains, in addition, sensor devices to determine the static pressure in the channel in order to enable a pressure difference control. The cylindrical belt channel and measuring channel are constructed in such a fashion that the flow rate and flow speed in the belt channel are approximately the same as the flow rate and flow speed in the measuring channel.

17 Claims, 3 Drawing Figures

FIG: 1

DEVICE FOR TESTING THE AIR PERMEABILITY OF AN ARTICLE

BACKGROUND OF THE INVENTION

The invention concerns an improved device to test the permeability to air of articles, called "test objects", in particular felts and screens used in machines and installations for manufacturing paper.

A prior art device of this type is known from EP-Pat. No. 0 096 31. This prior art device is designed as a movable instrument whose measuring channel is separated into two coaxial channel sections that define between each other a measuring aperture. The test object, for instance, a sheet made of fabric, a screen, or a felt, must be inserted into the measuring aperture and, subsequently, must be clamped tight. This prior art device is a technically complex construction which must be attached to a multitude of positions on the test object in order to arrive at permeability profiles, a procedure that takes a correspondingly long time. The test object must be clamped tight in order to obtain as uniform an air flow through the test object as possible and to avoid significant losses through leakage. By basing the design on a belt channel with equal pressure it is further possible to avoid most leakage losses that are caused by the surface structure of the test objects.

The purpose of the invention is to present an improved test device with the properties defined by the general characteristics of claim 1 that permit the determination of the permeability to air at different areas of a test object, rapidly and in a simple fashion, combined with the advantages of encompassing a wide range of values, covering at least a ratio of 50, and with high accuracy. The test device is usable with ease and without problems, it is appropriate for a large variety of objects having different permeability, and it is locally movable in order to allow for the acquisition of different permeability profiles. Finally, the device is applicable even in the case of slowly moving test objects.

The device permits the measurement of air permeabilities without requiring the test object to be clamped between the segments of the channel in which the air flow is measured. Instead, the invention makes it possible to attach channel segments to a single side of the test object, a procedure that has the advantage in that the device can be used for test objects which are only accessible from one side and/or which move continuously.

The test device can be constructed in such a fashion that it has a low weight and can be used manually with ease. This feature has the advantage that the test device allows for continuous measurements while it is being moved relative to a test object that itself is in motion. As a consequence, longitudinal and transverse measurements can be made.

In the process, the pressure drop in the case of diverse fabric permeabilities is automatically set to a predetermined value and kept at this mark. The replica of the natural flow through the test object, due to the screening of the flow in the measuring channel by the test object, by the air flow in the belt channel has the advantage to protect the air flow in the measuring channel from exterior influences and to make available an unavoidable amount of leakage air.

Thus, the test device permits the determination of air permeabilities for felts, screens, fabrics, and similar sheets in a short time. The permeability properties have a significant influence on various operating conditions of machines that are run with such felts or screens.

These and other objects of the invention will become apparent in light of the present specification and drawings.

DETAILED DESCRIPTION OF THE DRAWINGS

Figure 1:
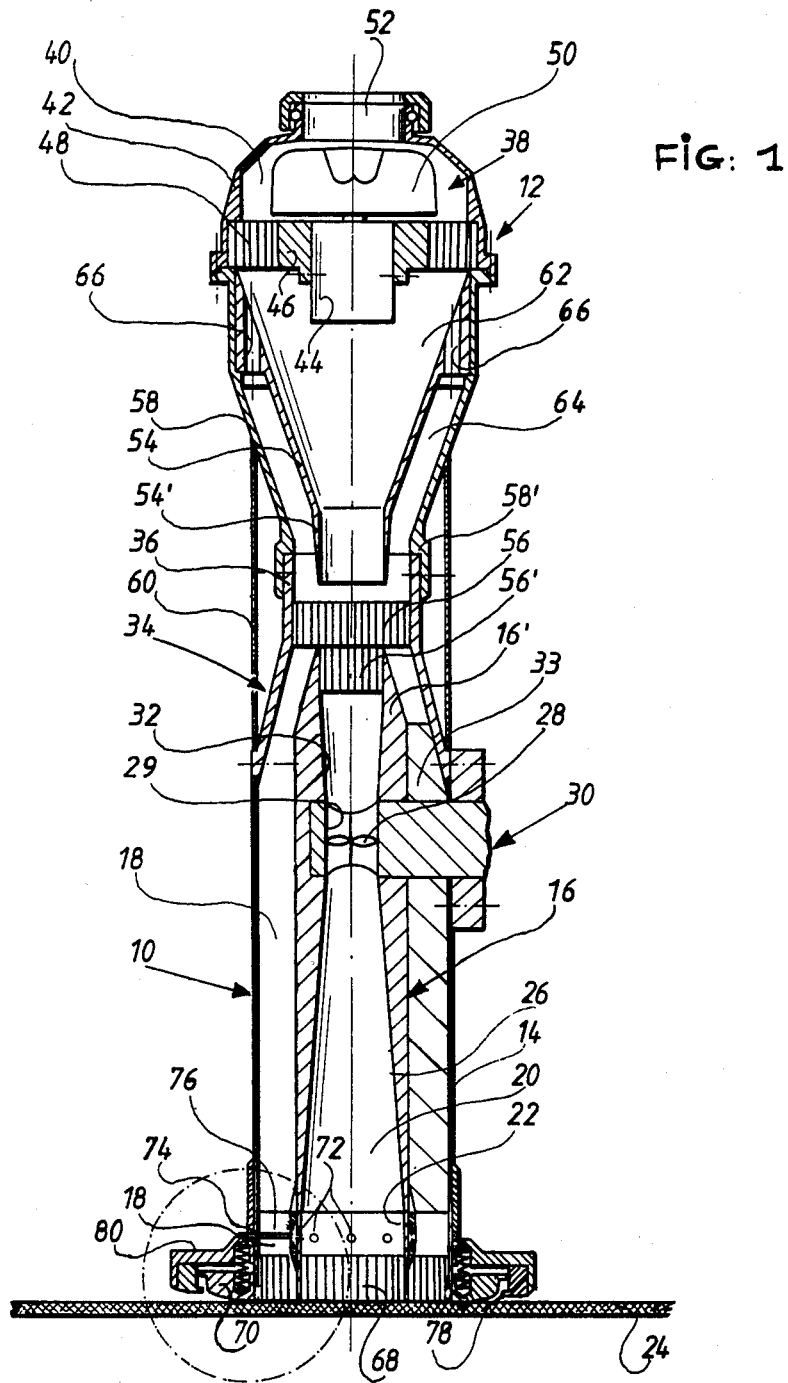
FIG. 1 of the drawings, is a longitudinal cross section view of the improved test device.

The design of the imposed test device is for a hand-held instrument. The device may obviously also be used as an instrument to be incorporated into a production machine, delivering air permeability profiles for a fabric sheet that is being tested. The device has a measuring tube which was given, as a unit, the designation (10). A fan attachment (12) is attached on this tube (10). The measuring tube (10) comprises a cylindrical casing (14) that forms, together with coaxially inserted casing inset (16), a belt channel (18) and defines an interior measuring channel (20).

Whereas the belt channel (18) forms a space that, in segments, is of a cylindrical form, the measuring channel (20) contains only a lower cylindrical channel segment (22), at least 20 mm long, whose interior circumference defines a measuring spot, for instance, on a fabric sheet (24) in a machine for manufacturing paper. The air permeability of the fabric sheet (24) is measured over the area of this measuring spot.

The cylindrical channel segment (22) turns into the channel segment (26) that is tapered upwards in the form of a cone. The fan wheel (28) of a fan-wheel anemometer (30) is placed into an adjacent channel segment (29).

Adjacent to the channel segment (29), there is a channel segment (32) that is flared by a small amount in the upward direction and in the form of a cone.

The lower cylindrical channel segment (22) of the measuring channel (20) preferably has a diameter of 35 mm and is at a length of the cylindrical longitudinal section (22) of the measuring channel (20) of at least 10 mm at most 4 mm thick, though preferably less than 2 mm thick. In this case, the resulting measuring spot has an optimal size for rating the test object. The channel segment (26), above segment (22), shows a diameter that preferably decreases down to a value of 18.2 mm. The ratio 35 mm to 18.2 mm of the diameters results in optimum conditions for a wide measuring range, if the sensitivity of, and the maximum flow velocity for, the fan-wheel anemometer (30) are taken into account, in particular, in the cases where dense felts and open dry screens form the test objects.

The ratio of the interior cross section of the lower cylindrical longitudinal segment (22) and the cross section of the measuring channel (20) proximate to the fan wheel anemometer wheel element (28) is in the range between 1.2 and 3.5, and preferably between 1.8 and 2.0.

The fan-wheel anemometer probe (30) is run radially outwards; in order to prevent flow separation inside the belt channel (18) when the air stream flows around the fan-wheel anemometer, a casing (33) is designed for the anemometer in the belt channel (18) that is designed for optimum flow characteristics. The air flow through the belt channel (18) must be equally distributed. To achieve this, a similar counterpart is provided at a position diametrically across from the casing (33). This counterpart is not shown in the diagram.

The design contains, for the same reason, two additional casings in the belt channel (18) that are offset by 90 degrees and serve as air-conducting elements.

A recording head (34) is put on the tube casing (14) into which the casing inset (16) enters with its upper end (16'). The recording head (34) is tapered in the upward direction in this area. A cylindrical segment joins the tapered segment and forms a mounting collar (36). The fan mount (12) is placed on this collar (36). The fan mount (12) contains in the upper portion a radial blower (38) in an air conduction chamber (40), the air conduction chamber being formed by the hood (42) put on the fan mount (12). The radial blower (38) contains a driving motor (44) which may be either a regulated dc motor or a synchronous ac motor. The motor is supported by a support ring (46) that is coaxial to the inner channel (20). The support ring (46) is supported by a flow rectifier (48) that may, for instance, be formed by a honeycomb lattice. A radial fan wheel (50), positioned above the flow rectifier (48), sits on the shaft of the driving motor (44). The fan wheel (50) sucks air through a central inlet (52) in the hood (42) and pushes it through the flow rectifier (48). Adjacent to the rectifier (48) is an inset (54) that is tapered in the form of a cone in the downward direction and whose end piece (54') is cylindrical and sticks into the collar (36). An additional flow rectifier (56), preferably formed by a honeycomb lattice, is placed into the upper end of the inner channel (20). At a minimum the segment (56') is necessary for measuring procedures in order to guarantee an irrotational flow in front of the fan wheel (28).

The casing inset (54) is radially surrounded by a portion of the casing (58) that, too, is tapered in the downward direction in the form of a cone. The ring-shaped end piece (58') of the casing (58) is attached to the mounting collar (36). A cylindrical handle piece (60) is formed between the head (34) and the portion (58) of the casing.

The inset (54) forms an inner flow channel (62) with a downwards tapered cross section, whereas inset (54) and the portion (58) of the casing form together the belt channel (64) that is tapered in the downwards direction in the form of a cone. The belt channel (64) is connected to the flow channel (62) by means of a ring of connecting openings (66) in the upper portion of the inset (54), positioned parallel to the axis. The air flow produced by the radial fan (38) is aligned by the flow rectifier (48) in such a fashion that the flow is partitioned according to the flow cross sections in the cylindrical channel segment (22) and the belt channel segment (18') that surrounds the channel segment (22). The ratio of the flow cross sections of the measuring channel (20) and the belt channel (18) is essentially kept constant, at a preferred value of 2.33, over the entire flow path from the cylindrical end piece (54') of the inset (16) to the orifice of the channel. In this manner it is guaranteed that the amount of air flowing through the measuring channel (20) suffices to protect the air flowing through the measuring channel (20) against external influences and to supply an unavoidable amount of leakage air.

It is desirable to equip the lower end of the measuring channel (20), to be attached to the test object (24), as well as the belt channel (18) in this area with a flow rectifier (68) which improves the laminar character of the emerging air flow and the efficiency of the pressure distribution for the purpose of radial sealing. The wall thickness between measuring channel (20) and belt channel (18) is preferably 1 mm in this area. In any case, it should be less than 5 mm in order to guarantee the screening effect the belt-channel flow has on the measuring-channel flow at the test object.

Figure 3:
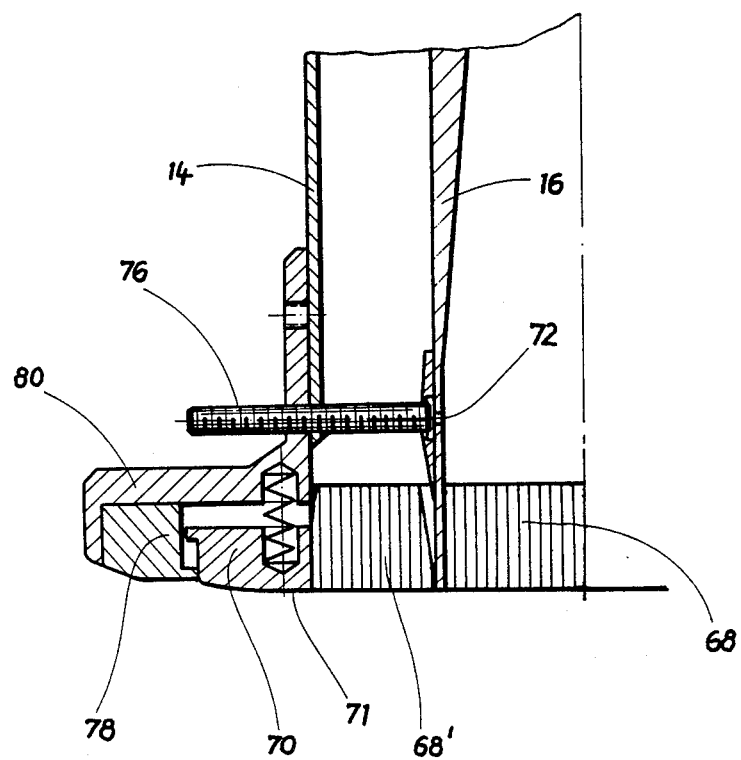
FIG. 3 of the drawings, shows an alternative version of the design shown in FIG. 2.

As far as the arrangement for the portion of the flow rectifier (68) which is to be located in the lower end of the belt channel (18) is concerned, this portion, identified as (68') in FIG. 3, is preferably designed in such as fashion that it is fastened, for instance, by means of an adhesive, to the interior circumference of the channel wall segment (70) and is flush with the lower face (71) of the channel wall segment (70). This arrangement makes sure that the flow rectifier portion (68') always rests on the fabric.

Figure 2:
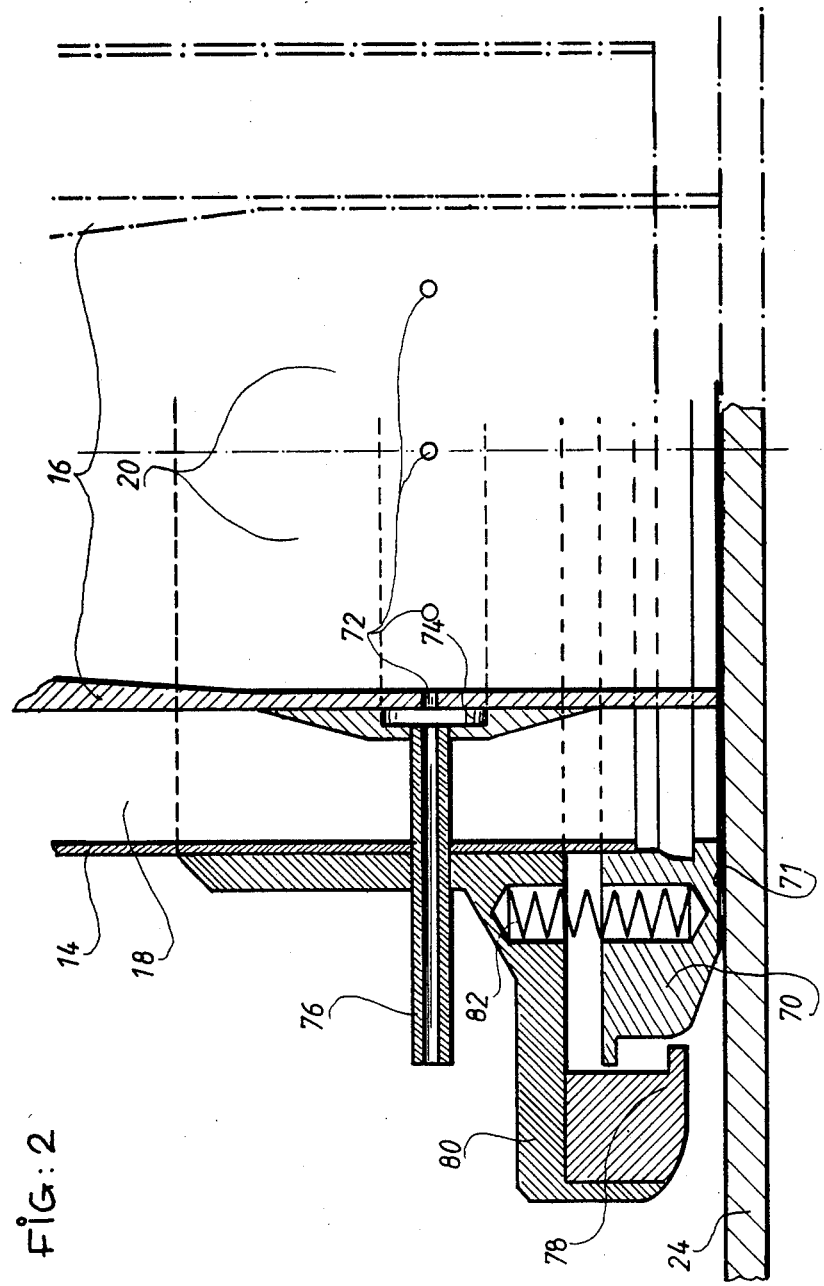
FIG. 2 of the drawings shows, on a magnified scale, the section of FIG. 1 that is marked by the dash-dotted circle.

The lower edge of the measuring channel (20) projects over the end piece of the cylindrical tube casing (14). As shown in FIG. 2, the lower end of the belt channel (18) is formed by an axially sealing ring (70), equipped with springs, that sits on the tube casing (14) with sufficient play to guarantee a perfect attachment of the lower ring area of the sealing ring (70) on the test object (24) even in the case of a tilt of the test device (10) with respect to the test object (24). In this manner it is ascertained that attaching the test device (10) with a tilt of a few degrees does not lead to changes in the recordings, that is, to errors in the measurements. In the case that the device (10) is attached from below, the sealing ring (70) is fixed by means of a ring-shaped stop (78) which forms part of a support (80) that is fastened to the tube casing (14) and used to support the pressure springs (82) acting on the sealing ring (70).

In order to obtain accurate test results it is important to ascertain that around the edge of the measuring spot no undefined amount of air is conducted above the test object instead of through the test object (24). In addition, it is important that the radial distance from the measuring channel (20) to the belt channel (18) is preferably between 1 and 2 mm so that this lateral flow is avoided. The ratio of the interior cross section of the lower cylindrical channel segment (22) of the measuring channel (20) and the interior cross section of the corresponding portion of the belt channel (18) should be larger than 0.5, and preferably larger than 1.0.

The permeability of the test object (24) is measured with the test device (10) by creating a well-defined pressure drop of, for instance, 1 mbar or 1.27 mbar, between the upper and the lower side of the test object (24) in the area of the measuring spot. The amount of air flowing per unit surface through the test object (24) at a given pressure difference depends on the type of fabric, its manufacture and dirtying, and the stretching of the test object. For this reason, the air permeability may sometimes drastically differ among measuring points. In our case, the pressure difference is generated, by means of blowing, as excess pressure with respect to the ambient pressure just above the test object (24). The volume flow in the measuring channel (20) is then measured and assigned to the free cross section of the measuring channel (20), that is, to the measuring spot. The measured value may be considered an average over the actual measuring area.

The static pressure difference that is generated in the measuring channel (20) is continuously measured. For this purpose, as shown in FIG. 2, several boreholes (72) are designed along the periphery of the lower cylidrical end piece (22) of the measuring channel (20) that penetrate the wall of the casing (16) and discharge into a collecting channel (74). The boreholes (72) have diameters of, preferably, 0.5 mm. but not more than 1 mm. The collecting channel (74) is connected, via the connecting channel (76), to an instrument, attached to the test device (10), which measures the static pressure difference. This continuous monitoring and controlling of the static air pressure in the measuring channel (20) makes sure that, in the case where the belt channel (18) starts leaking, for instance, if the attachment of the test device to the test object (24) had been done improperly, the amount of air is increased automatically according to the leakage, with the result that the air pressure in the area of the belt channel (18) drops insignificantly. The output of the radial blower (38) is correspondingly varied.

In summary, the test device works as follows:

The permeability to air of the test object (24) is measured by attaching the test device to the test object. The air flow, generated by the radial blower (38) and flowing through the two channels (18) and (20), meets the test object (24) in the area of the measuring spot and flows through the test object. In the process, the air flow drives a fan-wheel anemometer (30) which measures the flow rate. The test object (24) generates a pressure drop that depends on its permeability and the air volume that flows through per unit time and unit area. The pressure drop is held constant, for instance, at 1 mbar by controlling the air flow rate. The resulting changes in this flow rate are then recorded by the fan-wheel anemometer (30) for the purpose of analysis.

The foregoing description of the drawings merely explain and illustrate the invention and the invention is not limited thereto, except insofar as the amended claims are so limited as those skilled in the art who have the disclosure before them will be able to make modifications and variations therein without departing from the scope of the invention.

What is claimed is:

1. An improved device for testing the air permeability of an article, and particularly felts and screens associated with the manufacture of paper products, said device being of the type including a measuring channel through which air is propelled through utilization of a blower mechanism, and including measuring means for measuring the flow rate of air within said measuring channel, said air being propelled through a measuring area immediately adjacent the exposed surface of said article as a function of a controlled constant pressure differences created at said adjacent measuring area, said device further being of the type including a longitudinal positioned belt channel juxtaposed about said measuring channel in which said belt channel is additionally and operably directing propelled air from said blower mechanism, wherein said measuring channel and said belt channel each further include an orifice immediately adjacent to the exposed surface of said article, said improvement in said air permeability testing device further comprising:

said blower mechanism, said measuring channel, said measuring means for determining the rate of air flow in said measuring channel, said measuring area and said belt channel being integrated into a single operational testing device capable of being placed for air permeability testing to one of either of two sides of said article being tested;

said measuring means comprising a fan wheel anemometer having a fan wheel element operably positioned within said measuring channel for direct exposure to the air being propelled therewithin;

said measuring channel containing said fan wheel anemometer wheel element being operably connected to said orifice of said measuring channel immediately adjacent to said article through a channel section element, immediately adjacent said measuring channel orifice having a substantially cylindrical longitudinal construction, with said channel section further and operably being attached to a tapered longitudinal section emanating towards said measuring means in order to insure that said propelled air stream is unidirectional;

said air permeability testing device further including in at least one position upstream from said fan wheel element of said fan wheel anemometer, flow rectifier means for precluding the creation of rotational flows of propelled air onto the surface of said fan wheel element, said substantially cylindrical longitudinal section immediately adjacent said measuring channel area having one or more sensing means operably associated therewithin for measuring the extent of static pressure created at said area of measuring channel, for the purpose of regulating the rotational speed of the blower mechanism so as to maintain a desired static pressure value;

one or more of said belt channel and said measuring channel means being of such a geometric configuration so as to equalize the propelled air flow volume and velocity longitudinally conducted through said belt channel to the propelled air flow volume and velocity longitudinally directed through said measuring channel.

2. The improved air permeability test device according to claim 1 wherein said tapered longitudinal section of said measuring channel has an angular aperature, measured with respect to the interior walls of said measuring channel, of no greater than 18 degrees, preferably between 10 and 15 degrees.

3. The improved air permeability test device according to claim 1 wherein the ratio of the interior cross section of said cylindrical logitudinal section of said measuring channel and the cross section of said measuring channel proximate to said fan wheel anemometer wheel element is in the range between 1.2 and 3.5, preferably between 1.8 and 2.0.

4. The improved air permeability test device according to claim 1 wherein said cylindrical logitudinal section of said measuring channel containing said orifice has a minimum length of 20 mm.

5. The improved air permeability test device according to claim 1 wherein the wall of said cylindrical longitudinal section of said measuring channel further includes one or more boreholes and a collecting ring channel means juxtaposed thereto and perpendicular to said orifice of said measuring channel for measuring the static pressure in said cylindrical longitudinal section of said measuring channel.

6. The improved air permeability test device according to claim 1 further including first a flow rectifier means operably positioned in said cylindrical longitudinal section of said measuring channel proximate to said measuring area down stream of said sensing means for improving the laminar character of said air stream flow and the efficiency of the pressure distribution for purposes of radial sealing.

7. The improved air permeability test device according to claim 6 wherein said first flow rectifier means is operably positioned adjacent said orifice of said measuring channel and said orifice of said belt channel whereby said first flow rectifier means is fastened to the interior periphery of the outer wall of said belt channel flush with the lower face of said measuring channel and said belt channel.

8. The improved air permeability test device according to claim 1 further comprising adjustable sealing means operably attached to said orifice of said belt channel for maintaining the integrity of the placement of said orifice upons said article in the event said device is tilted away from a perpendicular orientation with respect to said article side.

9. The improved air permeability test device according to claim 1 wherein the ratio of the interior cross section of said orifice of said belt channel and the interior cross section of said corresponding orifice of said measuring channel is larger than 0.5, preferably larger than 1.0.

10. The improved air permeability test device according to claim 1 further comprising radial partition means longitudinally positioned between the outer periphery of said measuring channel and the inner periphery of said belt channel thereby partitioning said belt channel into longitudinal channels, with said radial partion means preferably positioned 90 degrees offset with respect to one another.

11. The improved air permeability test device according to claim 1 wherein the circumferential wall of said measuring channel which separates said measuring channel from said belt channel is at said cylindrical longitudinal section of said mesuring channel of at least 10 mm in length, and at most 4 mm thick, preferably less than 2 mm thick.

12. The improved air permeability test device according to claim 1 wherein said blower mechanism is a radial blower.

13. The improved air permeability test device according to claim 12 wherein said radial blower includes a radial fan blade element, and further inclulies a routing chamber means juxtaposed about said fan blade element, said routing chamber serving to reroute said air flow into an axial direction, and further includes a second flow rectifier means operably positioned between said routing chamber means and said fan wheel anemometer for producing an irrotational flow about said fan wheel anemometer.

14. The improved air permeability test device according to claim 13 wherein said second flow rectifier means further contains and carries said radial blower in such a manner as to obviate the need for support arms for said radial blower which would otherwise block or effect said air flow.

15. The improved air permeability test device according to claim 14 further including a flow channel positioned downstream of said second flow rectifier means, said flow channel being tapered in the shape of a cone in the direction of the flow of said air stream and juxtaposed by said belt channel in order to accurately distribute said air stream produced by said blower mechanism between said measuring channel and said belt channel.

16. The improved air permeability test device according to claim 1 in which said flow rectifier means includes a primary flow rectifier means operably positioned within said measuring channel between said fan wheel of said fan wheel anemometer and said blower mechanism and a secondary flow rectifier means operably positioned upstream from said primary flow rectifier means so that said air stream passes through said secondary flow rectifier means.

17. The improved air permeability test device according to claim 1 in which said blower mechanism can propel said air stream toward said article or alternatively draw said air stream away from said article.

* * * * *

UNITED STATES PATENT AND TRADEMARK OFFICE
CERTIFICATE OF CORRECTION

PATENT NO. : 4,730,481

DATED : March 15, 1988

INVENTOR(S) : Engelbert Schlipf

It is certified that error appears in the above-identified patent and that said Letters Patent is hereby corrected as shown below:

Col. 5, line 2, "cylidrical" should read -- cylindrical --.

Col. 7, line 39, "mesuring" should read -- measuring"--.

Signed and Sealed this

First Day of November, 1988

*Attest:*

DONALD J. QUIGG

*Attesting Officer*

*Commissioner of Patents and Trademarks*